United States Patent [19]

Lombardy wife Alric et al.

[11] Patent Number: 4,828,801

[45] Date of Patent: May 9, 1989

[54] DEVICE FOR DETECTING ON A NITROCELLULOSE SHEET THE PRESENCE OF MACROMOLECULAR COMPLEXES, SUCH AS ANTIGENS/ANTIBODIES

[75] Inventors: Monique Lombardy wife Alric, Clermont Ferrand; Michel Renaud, Le Cendre, both of France

[73] Assignee: Centre National de la Recherche Scientifique, France

[21] Appl. No.: 879,358

[22] Filed: Jun. 27, 1986

[30] Foreign Application Priority Data

Jul. 2, 1985 [FR] France ................... 85 10271

[51] Int. Cl.⁴ .................... B01L 3/00; B01L 11/00
[52] U.S. Cl. .................... 422/102; 422/101; 435/301; 436/809
[58] Field of Search .......... 436/809; 435/293, 300, 435/301; 422/69, 73, 100, 101, 102, 104, 48; 210/321.84, 456, 498

[56] References Cited

U.S. PATENT DOCUMENTS

| 2,073,991 | 3/1937 | Koser | 210/498 |
| 4,031,197 | 6/1977 | Marinkovich | 436/809 |
| 4,212,742 | 7/1980 | Solomon | 210/321.4 |
| 4,427,415 | 1/1984 | Cleveland . | |
| 4,526,690 | 7/1985 | Kiovsky et al. . | |
| 4,567,149 | 1/1986 | Sell et al. . | |

Primary Examiner—Michael S. Marcus
Attorney, Agent, or Firm—Parkhurst, Oliff & Berridge

[57] ABSTRACT

This invention relates to a device for detecting on a nitrocellulose-type sheet the presence of macro-molecular complexes, having:
  a bottom adapted to receive said nitrocellulose sheet,
  a plate adapted to rest on said nitrocellulose sheet applied on the bottom and having a plurality of parallel grooves that pass through said plate over the whole of its thickness and over the whole length of said grooves.

5 Claims, 6 Drawing Sheets

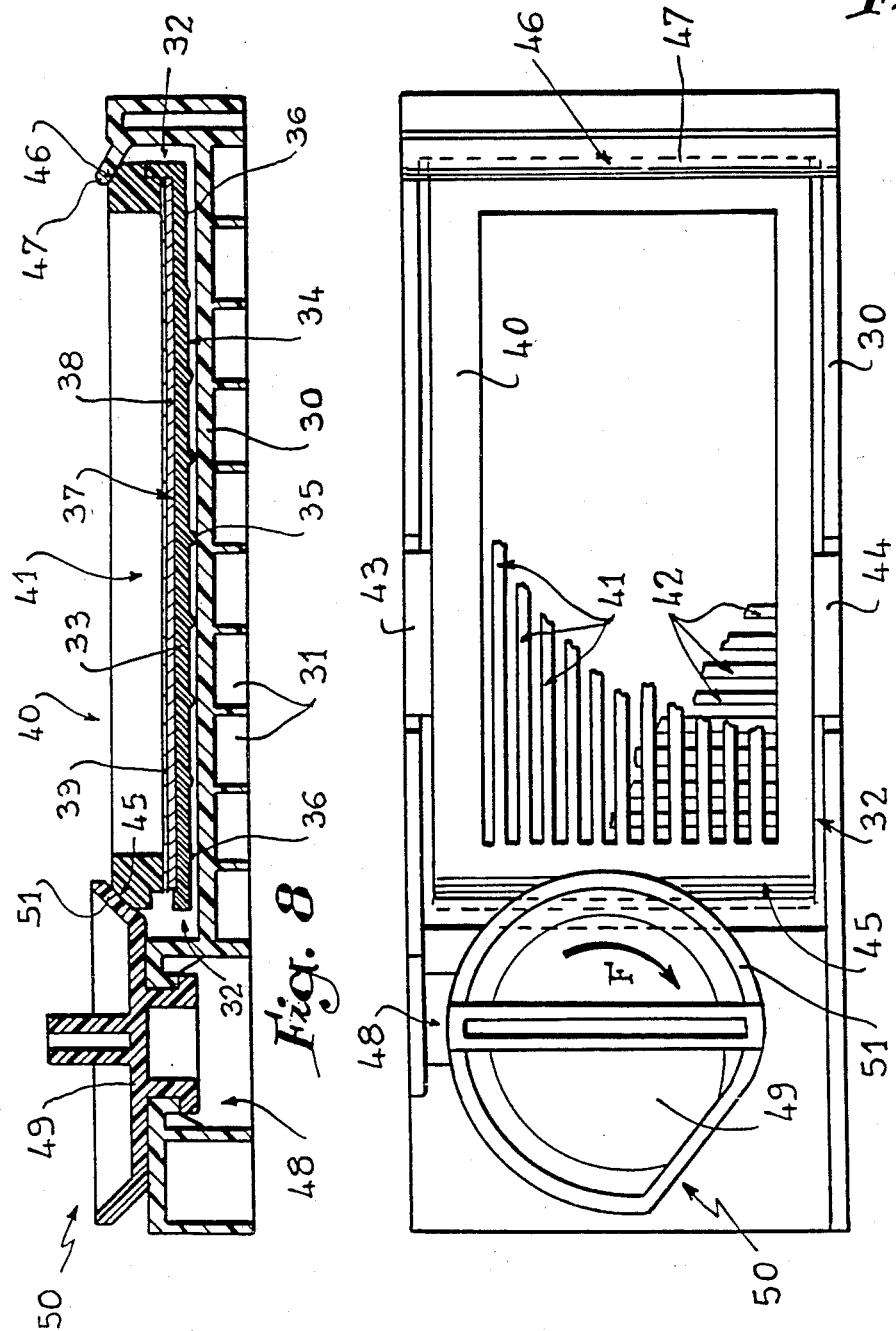

DEVICE FOR DETECTING ON A NITROCELLULOSE SHEET THE PRESENCE OF MACROMOLECULAR COMPLEXES, SUCH AS ANTIGENS/ANTIBODIES

BRIEF DESCRIPTION OF THE TECHNICAL FIELD

The present invention relates to a device for detecting the presence on a nitrocellulose-type sheet of macromolecular complexes, such as for example antigen-/antibody complexes; it also relates to a process implementing this device.

Although the invention is more particularly described in the following specification in its application to the detection of antigen/antibody complexes, it is in no way limited to this embodiment, since other reactants, and in particular other proteins, RNA and DNA, may also be used.

For detecting antigen/antibody complexes on a nitrocellulose-type sheet, a method, called "ELISA", is generally employed. A device carrying out this method is already known, essentially constituted by a plate of plastics material comprising a plurality of parallel, U-shaped wells which are individually filled with each of the reactants. Although this method is very widespread, this device requires control wells to make comparisons, and finally and especially, requires a large number of manipulations and a substantial quantity of reactants.

Apparatus have recently been described and even marketed, of which the upper plate is constituted by bottomless wells disposed as in the "ELISA" plates. This plate is deposited on a nitrocellulose sheet, itself placed on a second plate pierced with holes in register with the first, but of smaller diameter, then a vacuum is created on the bottom by suction, the assembly being maintained clamped for the whole of this operation (cf. for example U.S. Pat. No. 4,427,415 and European Patent EP-A-0118 735). However, this method is long to carry out and requires relatively well qualified personnel. In addition and in particular, this method has two major drawbacks, namely the impossibility of analyzing the components of the background noise and the specificity of certain responses.

"Analytical Biochemistry" 138, 119-124 (1984), describes a system constituted by:

an aluminium base in the form of a plate adapted to receive on its top a sheet of silicone rubber and a sheet of nitrocellulose;

a plate whose reverse side presents a plurality of parallel channels or grooves open only at their end (cf. also European Patent EP-A-0119 858).

This device for analysis is applicable only to the detection of BLOTS, i.e. biological macromolecules such as proteins, DNA or RNA, transferred onto the sheet of nitrocellulose after electrophoresis over gel, and not the detection of DOTS, this detection designating these same macromolecules disposed directly on the sheet of nitrocellulose. Moreover, the very design of this device causes the quasi-permanent presence of air bubbles in the channels, which, on the one hand, hinders filling of these channels and, on the other hand, and especially, disturbs the responses. It also causes leakages between the channels when the incubation time exceeds a few hours.

It is an object of the invention to overcome these drawbacks, and it relates to a detection device of the type in question which is easy and economical to produce, simple and rapid to manipulate, even with non-qualified personnel, enabling a small quantity of matter, even not perfectly purified, to be used, also enabling a large number of combinations to be made between the two reactants, and finally which gives responses without ambiguity and is therefore reliable.

BRIEF SUMMARY OF THE INVENTION

This device for detecting on a nitrocellulose-type sheet the presence of macromolecular complexes, comprising:

a bottom adapted to receive said nitrocellulose sheet, a plate adapted to rest on said nitrocellulose sheet applied on the bottom, comprising a plurality of parallel grooves, is characterized in that said parallel grooves pass through said plate over the whole of its thickness and over the whole length of said grooves.

In other words, the invention consists in no longer employing parallel grooves open only at their end, but parallel grooves open over their whole length and the whole thickness of the plate. In this way, after crossing of such plates, both DOTS and BLOTS may be studied and consequently, the number of combinations may be multiplied, which, heretofore, could not be done rapidly and reliably, on an economical scale. Thanks to this simple arrangement, the field of application and interest of this device may be considerably extended.

Advantageously, in practice:

the bottom, constituted by one or more parts, is in the form of a box in which is fitted the grooved plate whose top is in turn covered by a lid, the assembly: box, plate, lid being clamped together by appropriate closure members; these closure members, such as for example clamps or screws, must make it possible to distribute the pressure of matter uniformly over the whole surface of the grooved plate, must be practical, simple to manipulate and not be cumbersome;

a seal is disposed between the nitrocellulose sheet and the bottom of the box, constituted for example by a sheet of dampened paper or by an elastic membrane; in a first embodiment, this seal is constituted by a strongly absorbent, dampened paper; in a second advantageous embodiment, the sheet of dampened paper is disposed on a stack of dry elementary paper sheets, this allowing rapid adsorption of the first reactant on the nitrocellulose sheet; advantageously, the seal is a supple, elastic membrane, for example a membrane covered with silicone; similarly, this seal may be constituted by a stack of sheets of dampened paper covered with a water-tight sheet of the parafilm type;

in another configuration, the bottom of the box comprises a compartment adapted to be connected to a vacuum source in which is fixed another plate forming bottom pierced with through orifices, disposed, or not, opposite the through grooves of the first plate, a sheet of paper being interposed between this second bottom plate and the nitrocellulose sheet which is always in contact with the first grooved plate; in practice, the through orifices of the second plate are constituted by holes or grooves of small dimensions;

the bottom, plate and lid are made of machined or moulded plastic material;

the assembly comprises two plates with parallel open grooves, the direction of the grooves of the second plate being at right angles to the direction of those of the first plate;

parallel open grooves of a given plate may or may not be continuous;

the parallel open grooves have a width included between 1 and 4 mm; if this width is less than 1 mm, there is a risk of phenomena of capillarity on the walls; on the other hand, if this width is greater than 4 mm, for the same surface, the number of combinations able to be made is reduced unnecessarily and in addition, clamping is less efficient; although the height of the grooves, therefore of the plate comprising them is neither significant nor critical, it is important, on the contrary, that the length of these grooves be adapted to the desired use (BLOT or DOT). When used for BLOTS, the length of these grooves corresponds to that of the electrophoresis gel thanks to which the BLOTS are prepared, such as for example a polyacrylamide gel; finally, the distance between two successive parallel grooves must take into account the data of manufacture and of use in order to avoid untimely ruptures; economically, the grooved plate is moulded with appropriate draughts of the order of 1° to 3° for example.

The invention also relates to a process for implementing this device.

This process for detecting on a nitrocellulose-type sheet the presence of biological macromolecules, is characterized in that it consists:

in depositing a nitrocellulose-type sheet on at least one sheet forming seal disposed on a first bottom plate;

in covering this sheet with a second plate comprising a plurality of parallel grooves passing through this plate over the whole of its thickness and over the whole length of these grooves;

after having clamped said plates together, in filling these open grooves with a first reactant;

in leaving this first reactant to incubate on said nitrocellulose sheet, then in draining and rinsing the contents of the parallel open grooves;

after having removed the second plate, in leaving the nitrocellulose sheet to incubate, in order to saturate the aspecific sites;

in again covering the nitrocellulose sheet thus incubated with a third plate also comprising a plurality of parallel grooves traversing this plate over the whole of its thickness and over the whole width of these grooves, but of which the direction of the grooves is at right angles to the direction of the grooves of the second plate, so as to cross the direction of the grooves and consequently on the nitrocellulose sheet the interactions provoked by the grooves;

then, after having again clamped said plates together, in filling these open grooves with a second reactant;

in leaving to incubate, draining and rinsing then removing this third plate;

and, finally, in incubating, if necessary, the nitrocellulose sheet thus impregnated with the second reactant in order to saturate the aspecific sites before incubating it with solutions of developer sensors.

This process is particularly adapted to detection with CROSS-DOTS systems.

Advantageously, in practice:

the reactants are formed by solutions containing one or more reactants;

incubation is effected at the desired temperature, particularly from 4° to 37° C., the incubation time varying from some minutes to some hours;

draining is effected simply by turning the closed, clamped assembly over.

If the second and third plates have the same outer dimensions, after dismantling, after the first incubation, this plate is replaced after offsetting through 90° on the incubated nitrocellulose sheet, in order to obtain crossing on this nitrocellulose sheet of the interactions provoked by the grooves. If the second and third grooved plates are rectangular, the grooves of the second plate are disposed at right angles with respect to those of the third plate in order to obtain said crossings.

BRIEF DESCRIPTION OF THE DRAWINGS

The invention will be more readily understood on reading the following description with reference to the accompanying drawings, in which:

FIGS. 7 and 8 show another embodiment of the invention, seen in plan view (FIG. 7) and in longitudinal section (FIG. 8) respectively.

DETAILED DESCRIPTION OF PREFERRED EMBODIMENTS

Figure 1:
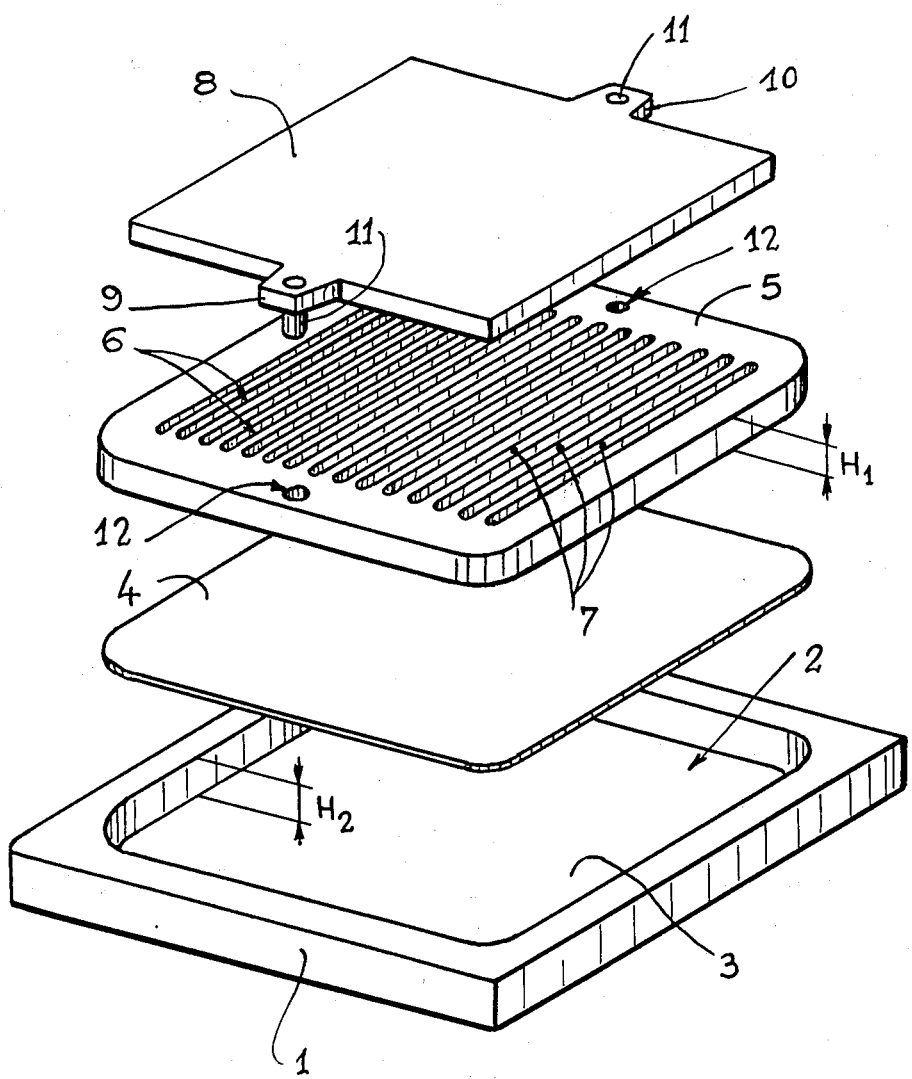
FIG. 1 is a summary, exploded view in perspective of the first device according to the invention.

As has already been stated, although the use described concerns the detection of antigen/antibody complexes, this embodiment is simply a preferred embodiment.

Referring now to the drawings, the device according to the invention essentially comprises three principal parts made of moulded plastics material, namely, respectively:

a box 1 in which is formed a compartment 2 on the bottom 3 of which will rest the sheet of paper 13 or an elastic waterproof membrane and the sheet of nitrocellulose 4;

a first plate 5 in which are formed a plurality of parallel through grooves 6, open over the whole height $H_1$ of this plate 5 and over the whole length of these grooves (cf. FIGS. 2 and 3) separated by inter-wells 7; the height $H_1$ of this first plate 5 is equal to the height $H_2$ of the compartment 2 of the box, whilst the length and width of this same first plate are slightly less than those of compartment 2, in order to be easily removable from this compartment 2;

a solid lid 8 which covers at least the grooved surface of plate 5, comprising two lateral lugs 9 and 10 which facilitate grip and on the reverse face of which are mounted pins 11 adapted to fit in orifices 12 provided to this end in the top of plate 5;

the assembly is maintained clamped by known closure members, such as clamps 14 (cf. 5) or the like.

In a version which has not been shown, particularly intended for diagnosis by non-professionals (such as farmers who can diagnose diseases in plants), the box is closed on the assembly of the first plate and the lid by a second lid formed in two lockable parts, this ensuring the action of closure and automatic clamping of the assembly.

In another version, more particularly intended for professionals, the bottom of the box is connected to a source of vacuum (not shown).

This device is used, in its application to the detection of antigen/antibody complexes, in accordance with the process defined hereinabove, care advantageously being taken to cover the bottom 3 of compartment 2 with a seal 13, such as a sheet of dampened, strongly absorbent paper or an elastic membrane on which the sheet of nitrocellulose 4 will therefore rest.

Figure 6:
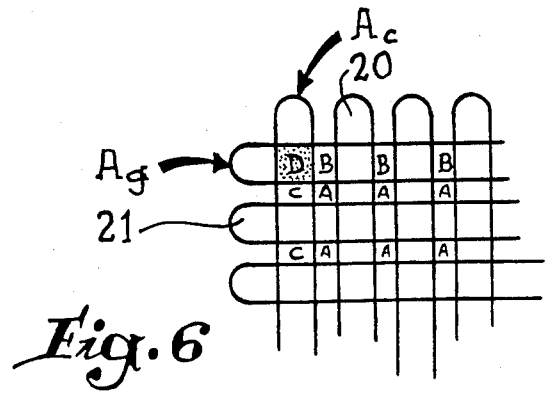
FIG. 6 is a summary representation to explain the operation of the device according to the invention.

Thus, thanks to the crossing of the characteristic grooved plates (cf. FIG. 6) and thanks to the large capacity of combinations, and the possibility of analyzing comparatively the origin of the background noise, this device makes it possible to effect a quantitative and qualitative analysis of these numerous parameters influencing the formation and analysis of the antigen/antibody complexes. According to the results obtained (cf. FIG. 6), four regions on the nitrocellulose sheet 4 may thus be defined. These four regions are schematized by references A, B, C and D and contribute in complementary manner to estimate the different components of the background noise, therefore for analyzing without ambiguity the antigen/antibody response. Region A corresponds to the background noise encountered in the absence of antigens and antibodies since this zone has not been affected in any way. Region B enables the background noise due to the antigen to be assessed, whilst region C enables the background noise due to the antibody to be assessed. In the absence of any specific antigen/antibody reaction, the maximum intensity due to the aspecificity is therefore the sum of the intensities of regions B and C. By comparison, the intensity of the response of region D gives the specificity thereof.

In the industrial embodiment shown in FIGS. 7 and 8, the moulded plastic assembly essentially comprises a base 30 with cells 31, similar to 2, which presents on the top and to the right a compartment 32 similar to 3. In this compartment 32 is housed an interposed sole 33 whose lower face 34 presents semi-spherical protuberances 35, 36 respectively, moulded therewith, of which the height decreases from the centre 35 towards the edge 36. The upper face 37 of this interposed sole 33 comprises a housing in which is applied the characteristic seal 38 similar to 13 such as an elastic membrane or a sheet of dampened paper. On this seal 38 is then applied the sheet of nitrocellulose 39 similar to 4.

As beforehand, the characteristic grooved plate 40 comes into abutment on this stack 39, 38, 33. The characteristic plate 40 comprises, as has already been stated, parallel grooves 41, 42 open over their whole height and whole length.

The progressive semi-spherical protuberances 35, 36 ensure a better seal of the assembly and facilitate a slight lateral slide of the characteristic grooved plate 40.

Lateral notches 43, 44 facilitate positioning and withdrawal of the grooved plates 40 in the compartment 32 thanks to lugs designated by the same references 42, 44 provided to this end when the characteristic plate 40 is moulded.

The plate 40 presents at each of its ends inclined planes 45 and 46 respectively which ensure blocking by cooperating with the closure member generally designated by reference 50. The right-hand inclined plane 46 cooperates with an integral fixed tongue 47 forming stop, fast with base 30. On the other hand, the left-hand inclined plane 45 cooperates with the closure member 50 proper, characteristic of the invention.

This closure member generally designated by reference 50 positioned to the left of the characteristic plate 40 slides in a slide way 48 provided to this end in the base 30. The closure member comprises an asymmetrical manoeuvring knob 49 whose raised periphery 51 forms a cam abuting on the corresponding inclined plane 45. In this way, by turning the knob 49 in the direction indicated by arrow F, the raised lip 51 abuts on the inclined plane 45. Simultaneously, the characteristic plate 40 compresses the interposed sole 37 and slides slightly on the sheet of nitrocellulose 39 without scratching it.

The partial lines symbolized in FIG. 7 represent the crossing of the characteristic parallel grooves 41, 42 respectively of two respective plates 40 which, after crossing, enable the intensity of the responses to be assessed.

As has already been stated, FIGS. 9 to 14 show different embodiments of the characteristic plates 5 of the invention, which may be crossed with respect to one another.

Figure 2:
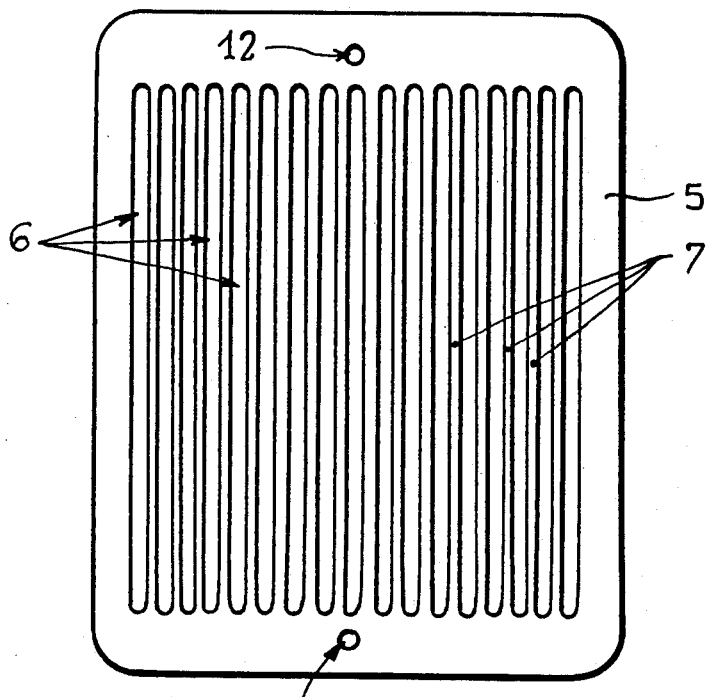
FIGS. 2 and 3 show the grooved plate characteristic of the invention, seen in plan view (FIG. 2) and in section (FIG. 3).
Figure 3:
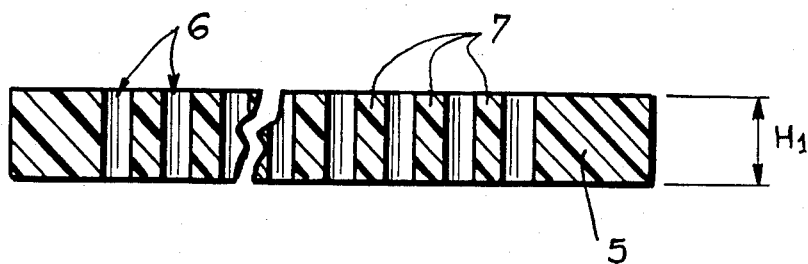
Figure 4:
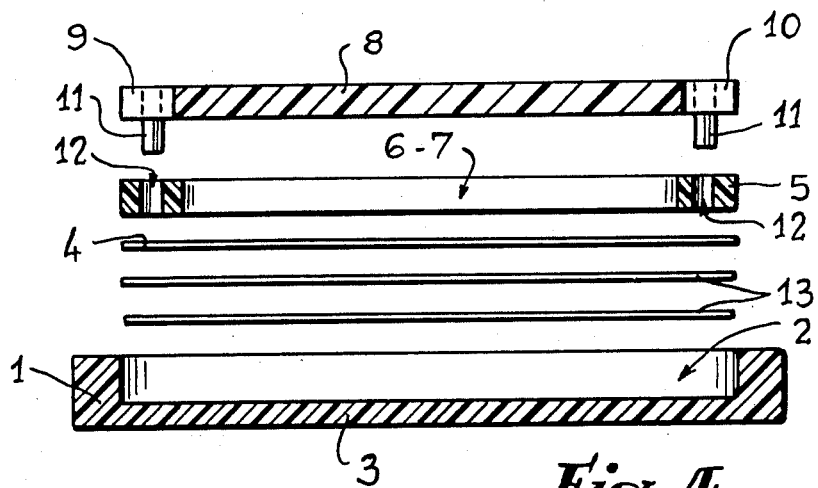
FIG. 4 is a view in section of the device of FIG. 1 in which all the elements have been shown exploded, whilst in FIG. 5 these same elements are in position.
Figure 5:
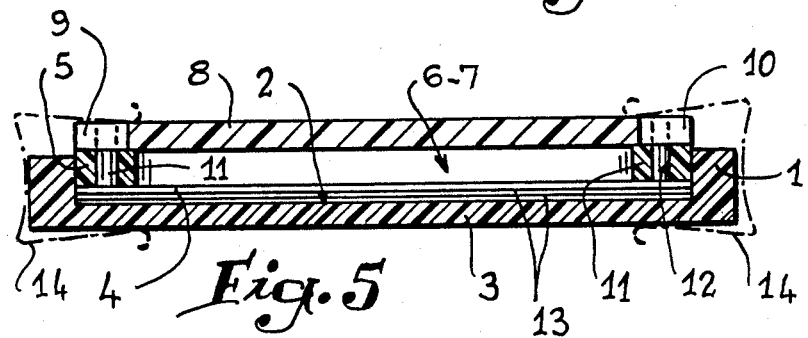
Figure 9:
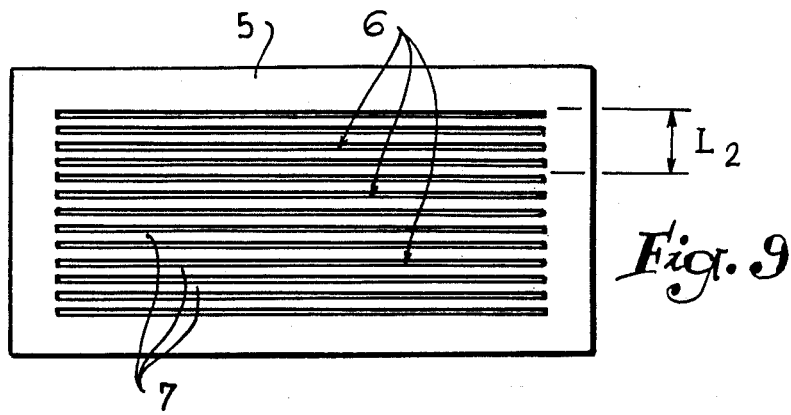
FIGS. 9 to 14 show in plan view different embodiments of the plates characteristic of the invention.
Figure 10:
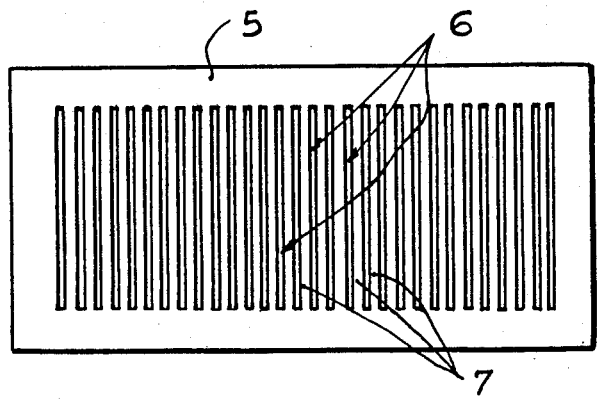

Plates 5 in FIGS. 9 and 10 correspond substantially to plates 5, illustrated in FIGS. 1, 2 and 3, intended to be crossed during use.

Figure 11:
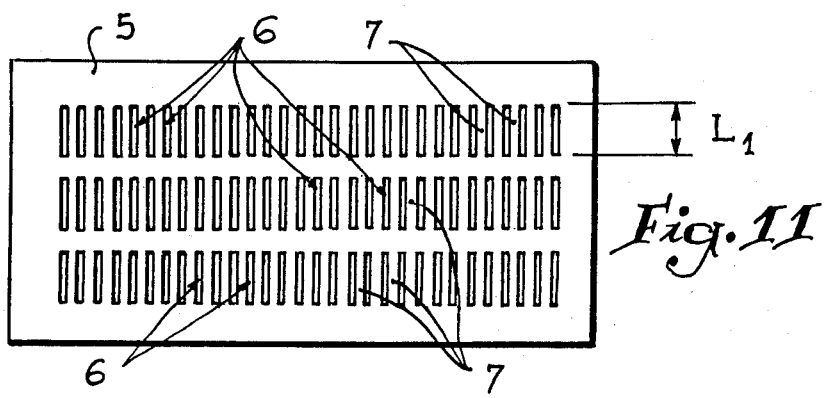
Figure 12:
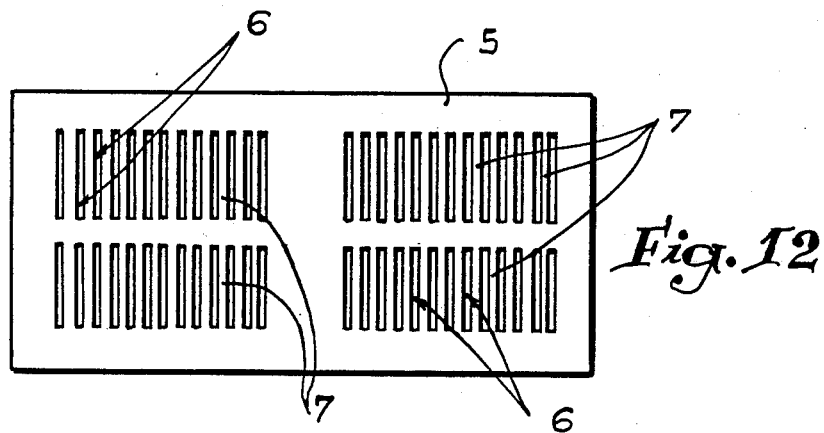

FIGS. 11 and 12 illustrate a variant of the plate 5 according to FIG. 10 in which the grooves 6 are of equal lengths but discontinuous and are grouped in groups of two (FIG. 12) or three (FIG. 11). The length $L_1$ of the discontinuous grooves is equal to the space $L_2$ between a whole number of grooves 6 of the other plate. This arrangement makes it possible considerably to increase the number of combinations to be tested in one experiment. For example, if the two plates shown in FIGS. 11 and 12 are crossed with the plate illustrated in FIG. 9, $(90 \times 3 = 270$ combinations) and $(52 \times 6 = 312$ combinations) are respectively obtained.

Figure 13:
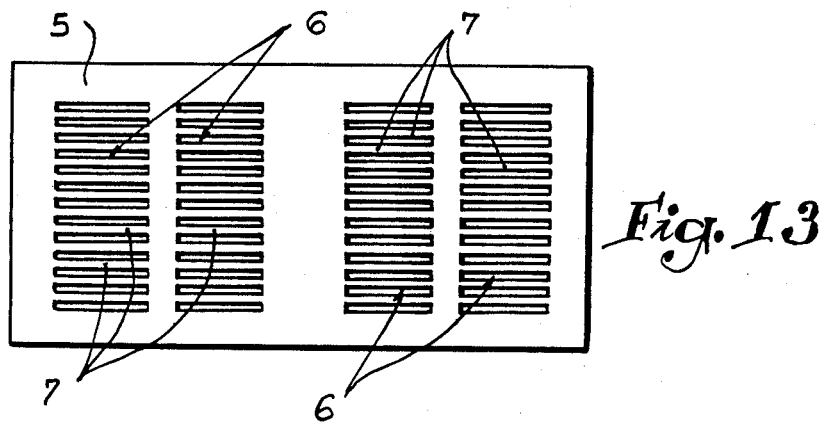

FIG. 13 shows an alternative of FIG. 9 intended to cooperate with the plates according to FIGS. 10, 11 and 12.

Figure 14:
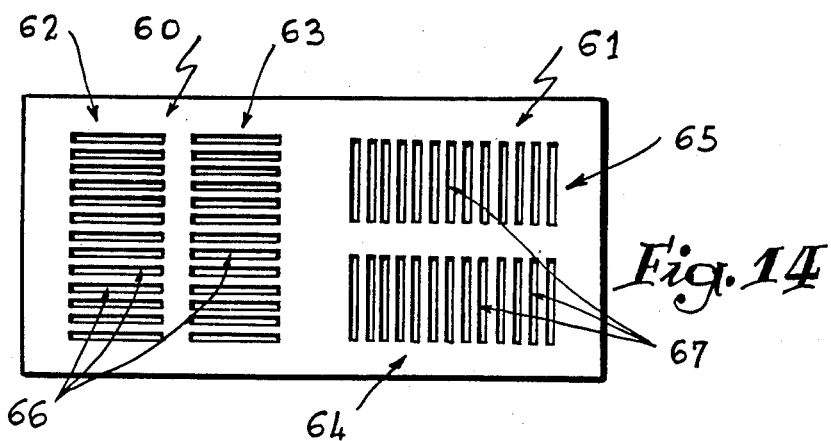

The plate illustrated in FIG. 14 comprises two series 60, 61 respectively of parallel grooves at right angles to each other, each grouped in two groups 62 to 65 of two sub-groups 62, 63 and 64, 65. These parallel grooves 66 and 67, similar to 6, are in equal numbers and all have equal lengths and widths. In this way, one and the same plate according to FIG. 14 may be used for a CROSS-DOT experiment. It simply suffices to pivot the plate through 180° from one phase to the other. It goes without saying that numerous other combinations of groups of parallel grooves may be made without departing from the scope of the present invention.

The device and process according to the invention comprise numerous advantages over those known heretofore. For example:

concerning the apparatus:
reduced cost,
the fact that the box may receive different plates, this increasing the possibilities of combinations,
the absence of leakages, therefore absence of contamination;
concerning the process:
the fact of being rapid and easy to manipulate with a reduced number of operations, without requiring qualified personnel,
the possibility of using the reactants in any order,
an excellent reproducibility since all the squares resulting from the same crossing have the same intensity, the direct elimination of the false positives, the possibility of obtaining a direct analysis of the response and thus of comparing affinities, a saving in the quantity of reactants (by 20 to 30 times depending on the number of crossed grooves), finally, with respect to the two processes mentioned in the preamble:

on the one hand, the number of combinations of first and second reactants in one experiment is much higher than that of the existing systems, since it is more than doubled, and even increased tenfold, depending on the use;

in addition and in particular, the possibility of making, as already stated, a direct analysis of the contribution of each of the background noises and of the specific signal of the interaction of the reactants, vs. the possibility of assessing immediately and directly, without an additional experiment, whether the second reactant is specific, which thus enables a diagnosis to be made.

A device is thus obtained with multiple possibilities for the detection of very complex macromolecular reactants, particularly biological macromolecules, such as proteins (antigen/antibody complexes, DNA/RNA, ...) in any combination. This device and method are thus particularly adapted to medical, agricultural, veterinary, biochemical diagnosis by qualified professionals or even by non-specialized users.

What is claimed is:

1. A device for detecting the presence of macromolecular complexes on a nitro-cellulose sheet, comprising:

a bottom member having the form of a box in which is formed a compartment adapted to receive a nitrocellulose sheet;

a plate adapted to rest on a surface of a nitrocellulose sheet opposite another surface of the nitrocellulose sheet in contact with said compartment of said bottom member, said plate comprising a plurality of parallel grooves directed to said sheet, said grooves being open over a whole thickness of said plate and over the whole length of said grooves;

a lid which covers at least the free openings of the grooves opposite to a nitrocellulose sheet; and means for clamping tightly together said bottom member, a nitrocellulose sheet and, said plate, further comprising a sole adapted to be interposed between the bottom of said compartment and a nitrocellulose sheet, the surface of said sole which is directed towards said bottom presenting protuberances whose height decreases from the center towards the edge.

2. The device of claim 1, wherein the parallel open grooves of the said plate are discontinuous but of equal length.

3. The device of claim 1 wherein said box comprises:

a first part which comprises said compartment having an interposed sole adapted to be housed between the bottom of said compartment and a nitrocellulose sheet, such that the surface directed towards said bottom of said compartment presents protuberances whose height decreases from the centre towards the edge, and the opposite surface receives a seal on which is applied said nitrocellulose sheet, and on which is in turn applied said plate comprising a plurality of parallel grooves, a second part, contiguous to the first, which receives a closure member comprising an asymmetrical rotatable maneuvering knob whose periphery forms a cam and abuts on the edge of the grooved plate to block the latter in the compartment.

4. The device of claim 3, wherein two opposite edges of the grooved plate comprise inclined planes, one of these inclined planes cooperating with a tongue forming stop, fast with the base, the other, opposite inclined plane cooperating with the inclined periphery of the rotatable maneuvering knob.

5. The device of claim 1, further comprising a second plate having a plurality of parallel grooves open over the whole thickness of said second plate and over the whole length of said grooves, said second plate adapted to be crossed with said first plate such that the direction of said grooves of said second plate is perpendicular to the direction of said grooves of said first plate.

* * * * *